US005772616A

United States Patent [19]
Competiello et al.

[11] Patent Number: 5,772,616
[45] Date of Patent: Jun. 30, 1998

[54] PORTABLE WATER APPARATUS FOR CLEANING THE TEETH AND GUMS

[76] Inventors: Joseph W. Competiello; Sandra L. Competiello, both of 10 Mark La., Milton, Mass. 02186

[21] Appl. No.: 858,930

[22] Filed: May 20, 1997

[51] Int. Cl.$^6$ .................................................. A61G 17/02
[52] U.S. Cl. .............................................. 601/165; 285/8
[58] Field of Search ............................ 601/165; 433/80; 285/8

[56] References Cited

U.S. PATENT DOCUMENTS

| | | | |
|---|---|---|---|
| 3,593,707 | 7/1971 | Pifer | 601/163 |
| 3,690,314 | 9/1972 | Trupp et al. | 601/165 |
| 4,135,501 | 1/1979 | Leunissan | 433/80 |
| 4,265,229 | 5/1981 | Rice et al. | 601/165 |
| 4,903,687 | 2/1990 | Lih-Sheng | 601/165 |
| 4,941,459 | 7/1990 | Mathur | 601/165 |
| 5,095,893 | 3/1992 | Rawden, Jr. | 601/165 |
| 5,231,978 | 8/1993 | Kao et al. | 601/165 |
| 5,273,428 | 12/1993 | Fischer | 433/80 |
| 5,387,182 | 2/1995 | Otani | 601/165 |
| 5,484,281 | 1/1996 | Renow et al. | 433/80 |

*Primary Examiner*—John J. Wilson
*Attorney, Agent, or Firm*—John D. Gugliotta

[57] ABSTRACT

A device for cleaning teeth and gums is provided. The device has an improved adapter that is easily connected to and disconnected from a variety of different faucet nozzles. A plurality of tips may be used with the invention.

9 Claims, 3 Drawing Sheets

PORTABLE WATER APPARATUS FOR CLEANING THE TEETH AND GUMS

RELATED APPLICATIONS

The present invention is a continuation of Disclosure Document Registration Number 408,134 filed on Oct. 29, 1996.

FIELD OF THE INVENTION

This invention relates to a device for improving dental hygiene. More particularly, the invention relates to a user-friendly, portable unit for cleaning teeth and gums.

BACKGROUND OF THE INVENTION

Various methods and apparatus have been and are being used for cleaning the teeth and oral cavity. The most generally used apparatus is the conventional toothbrush containing a dentifrice in the form of a paste or gel. Apparatus have also been developed for applying a jet of water against the teeth and gums. This method is often preferable to the use of a brush and is recommended to be performed in addition to cleaning with a brush. The jet stream of water is useful because it can penetrate crevices and spaces between teeth and dental appliances which cannot be reached by a brush, thereby dislodging food particles and plaque which would otherwise not be removed. The stream of water is also useful for massaging the gums of the user.

Apparatus for providing a jet stream of water for dental hygiene purposes are known. For example, U.S. Pat. Nos. 4,265,229 and 5,484,281 describe oral hygiene devices for attachment to a shower head assembly for cleansing the teeth and the oral cavity with a jet stream of water while showering. While these devices have several drawbacks, the fact that the user must be in the shower during use readily distinguishes the present invention. Faucetconnected devices for delivering a jet stream of water are also known, such as those described by U.S. Pat. No. 3,593,707, U.S. Pat. No. 3,690,314, U.S. Pat. No. 4,941,459, U.S. Pat. No. 5,095,893, and U.S. Pat. No. 5,387,182. While the devices disclosed by these patents avoid the need for the user to stand inside a shower, these devices suffer because they do not include a universal adapter which is easily connected to and disconnected from a widespread number of variably-sized faucets.

The foregoing demonstrates that there is a need for a device that provides a jet stream of water which includes an adapter which allows for quick attachment and detachment of the device to a faucet and is significantly cheaper to manufacture and easier to use compared to the devices known in the art.

BRIEF SUMMARY OF THE INVENTION

The device described by the invention is a user-friendly, flossing device that uses water to clean teeth and gums by removing plaque and food from between the teeth and around the gums. The device provides an adapter which forms a liquid tight seal and may be easily connected and disconnected to any style faucet. In one embodiment, the adapter takes the form of a funnel and latch combination. A flexible hose is provided which connects the funnel with the handle and tips. The tips are interchangeable allowing different people to use the invention for various applications.

The latch of the invention may include a stirrup which engages the faucet. The latch may also include a flat rubber plate with a raised connection orifice for communication with the nozzle of a faucet. An adjustable thumb screw with a cushioned swivel head may also be provided.

The device of the invention may be used at home or taken on travel and used in hotels or other locations due to its portability and ease of connection and disconnection. Advantageously the invention has no electrical parts and very few moving parts. Thus maintenance relating to pumps and motors is eliminated.

DETAILED DESCRIPTION OF THE PREFERRED EMBODIMENT

Figure 1:
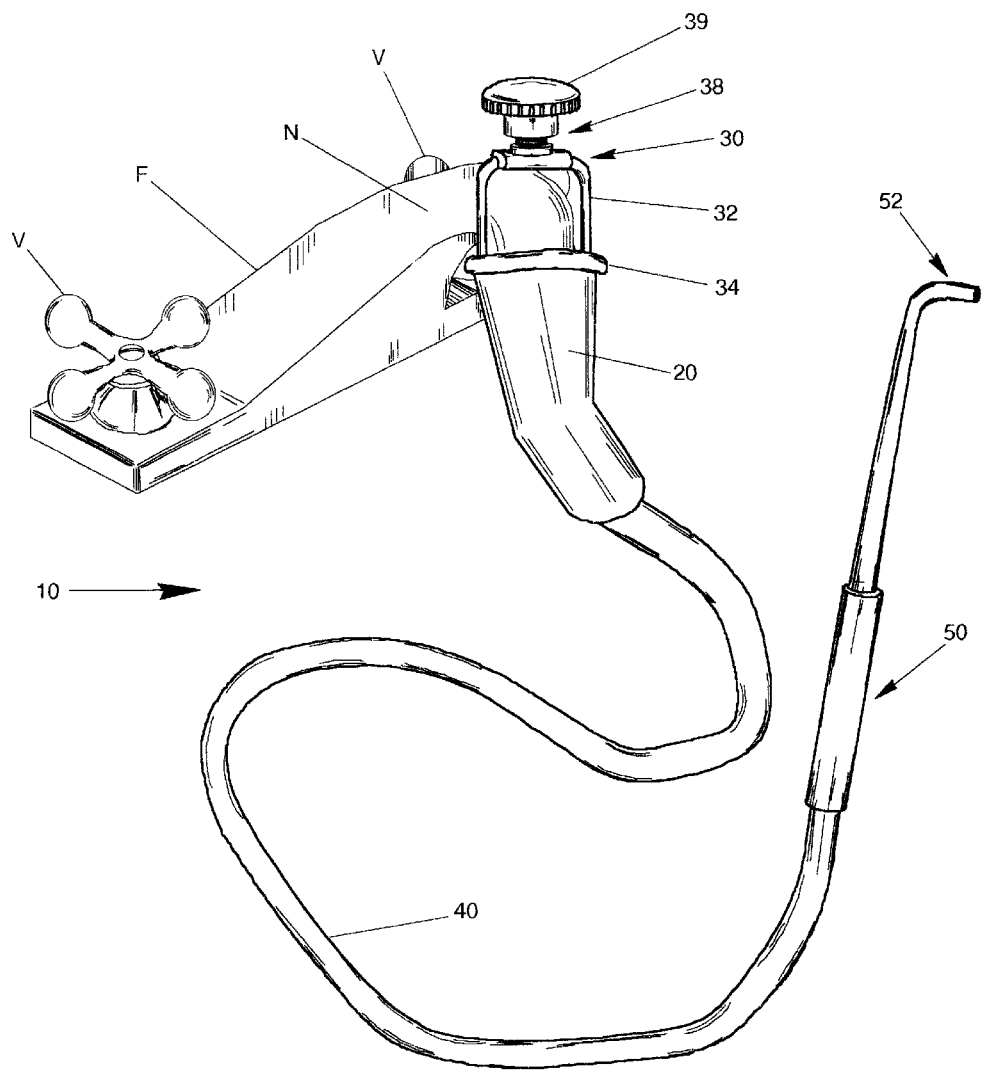
FIG. 1 is a perspective view of an apparatus constructed according to the principles of the invention.
Figure 2:
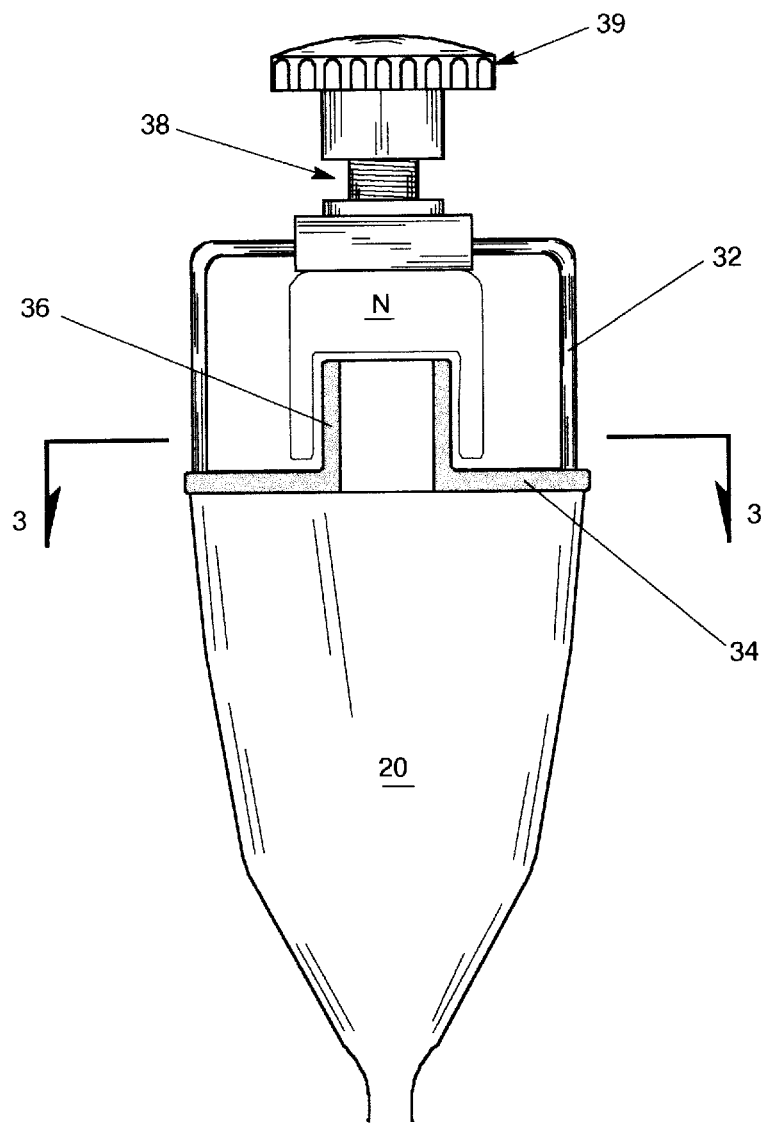
FIG. 2 is a cross sectional view of one embodiment of the invention.
Figure 3:
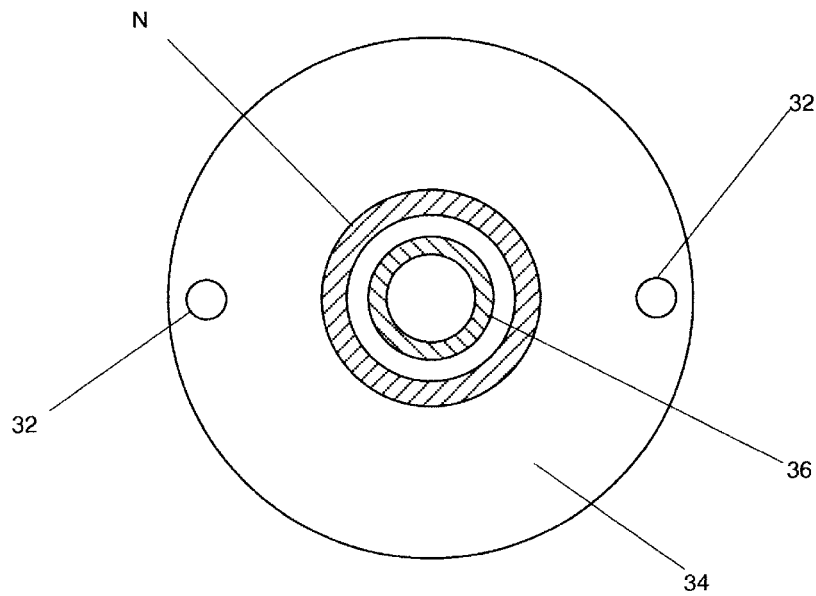
FIG. 3 is a cross sectional view of the embodiment depicted in FIG. 2 taken along line 3—3.

FIG. 1 illustrates one embodiment of the invention where a portable water apparatus for cleaning teeth and gums 10 is generally shown connected to the outlet of a water faucet or spigot F. In this embodiment, funnel 20 may be held in fluid communication with faucet F via latch 30. Funnel 20 may also communicate with tubing 40 and ultimately handle 50 and tip 52.

In the embodiment shown in the Figures, latch 30 is formed as a stirrup 32 which slips over the faucet nozzle N. Plate 34 may extend between the extensions of stirrup 32 below nozzle N to form a fluid connection between the funnel 20 and the faucet F. Plate 34 may be made of a variety of materials such as rubber, thermoplastic and metal or may be constructed of a combination of materials. In one embodiment, a plate 34 is made of rubber and has a metal base. Plate 34 may also have a raised orifice 36 which facilitates the effectiveness of the connection between plate 34 and nozzle N. An adjustable thumb screw 38 may be attached to the top of stirrup 32. When screw 38 is positioned above nozzle N, head 39 may be tightened to securely hold the funnel 20 on the faucet nozzle N. Head 39 may be cushioned for ease of manipulation by the user. Thus, in this embodiment of the invention a liquid tight seal may be attained between 10 and faucet F without the requirement of a threaded connection with nozzle N.

After adapter 20 is secured to faucet F, water from faucet F may be forced through adapter 20 and tubing 40 by manipulating faucet valves V. Tubing 40 is preferably flexible and may be designed to have a narrow diameter so that high water pressures may be created within the tubing 40. After water flows from the tubing 40 to handle 50 it is sprayed from tip 52. Tips 52 are interchangeable and are conventionally known in a variety of designs. For example, U.S. Pat. Nos. 3,593,707, 5,273,428, and 5,484,281, the disclosures of which are incorporated by reference, describe a variety of useful tips 52 which may be attached to handle 50. Tips 52 other than those useful for flossing are also contemplated by the invention. For -example, such tips 52 may include a spray attachment for sink cleaning, a hose tip for filling containers, and a connection to fill water beds.

While the preferred embodiments of the invention have been shown, illustrated, and described, it will be apparent to those skilled in this field that various modifications may be made in these embodiments without departing from the spirit of the present invention. For that reason, the scope of the invention is set forth in the following claims.

What is claimed is:

1. A device for cleansing and massaging the teeth and gums which is connected to the nozzle of a faucet, said device comprising:

a funnel having a plate for fluid communication with the faucet nozzle;

tubing in fluid communication with said funnel;

a handle in fluid communication with said tubing;

a tip in fluid communication with said handle; and a latch for holding the funnel in fluid communication with the nozzle, wherein said latch comprises a flat rubber plate with a raised connection orifice for communication with the nozzle of the faucet.

2. The device of claim 1 further comprising a plurality of tips wherein said tips are interchangeable.

3. The device of claim 1 wherein said funnel is designed to provide a liquid tight connection with the faucet.

4. The device of claim 1 wherein said latch comprises a stirrup that engages the faucet.

5. A connecting device for forming a liquid tight seal with the nozzle of a faucet, comprising:

a funnel having a plate for fluid communication with the faucet nozzle;

a latch for holding the funnel in fluid communication with the nozzle, wherein said latch comprises a flat rubber plate with a raised connection orifice for communication with the nozzle of the faucet.

6. The connecting device of claim 5 further comprising tubing in fluid communication with said funnel.

7. The connecting device of claim 6 further comprising a handle in fluid communication with said tubing.

8. The connecting device of claim 7 further comprising a tip in fluid communication with said handle.

9. The connecting device of claim 8 further comprising a plurality of tips wherein said tips are interchangeable.

* * * * *